(12) United States Patent  
Barnes

(10) Patent No.: US 6,314,961 B1
(45) Date of Patent: Nov. 13, 2001

(54) ADJUSTABLE EAR SUPPORT APPARATUS

(76) Inventor: Jason Lee Barnes, 1701 W. Wickieup, Phoenix, AZ (US) 85027

( * ) Notice: Subject to any disclaimer, the term of this patent is extended or adjusted under 35 U.S.C. 154(b) by 0 days.

(21) Appl. No.: 09/312,774

(22) Filed: May 14, 1999

(51) Int. Cl.[7] ................................................. A61F 11/00
(52) U.S. Cl. ............................................ 128/864; 128/866
(58) Field of Search .................... 128/864–868; 129/96

(56) References Cited

U.S. PATENT DOCUMENTS

| 3,257,990 | 6/1966 | Robertson et al. . |
| 3,970,080 | 7/1976 | White . |
| 4,221,189 | * 9/1980 | Olvera .................................. 128/866 |
| 4,250,875 | 2/1981 | Marsh et al. . |
| 4,275,715 | 6/1981 | Wolfe . |

* cited by examiner

*Primary Examiner*—Michael A. Brown
(74) *Attorney, Agent, or Firm*—Parsons & Goltry; Michael W. Goltry; Robert A. Parsons

(57) ABSTRACT

Apparatus for supporting and protecting newly cropped ears of an animal including first and second ear support apparatus each engagable with one of the newly cropped ears and a bridge interconnecting the first ear support apparatus with the second ear support apparatus, wherein the bridge is adjustable for adjusting the distance between the first and second ear support apparatus.

23 Claims, 4 Drawing Sheets

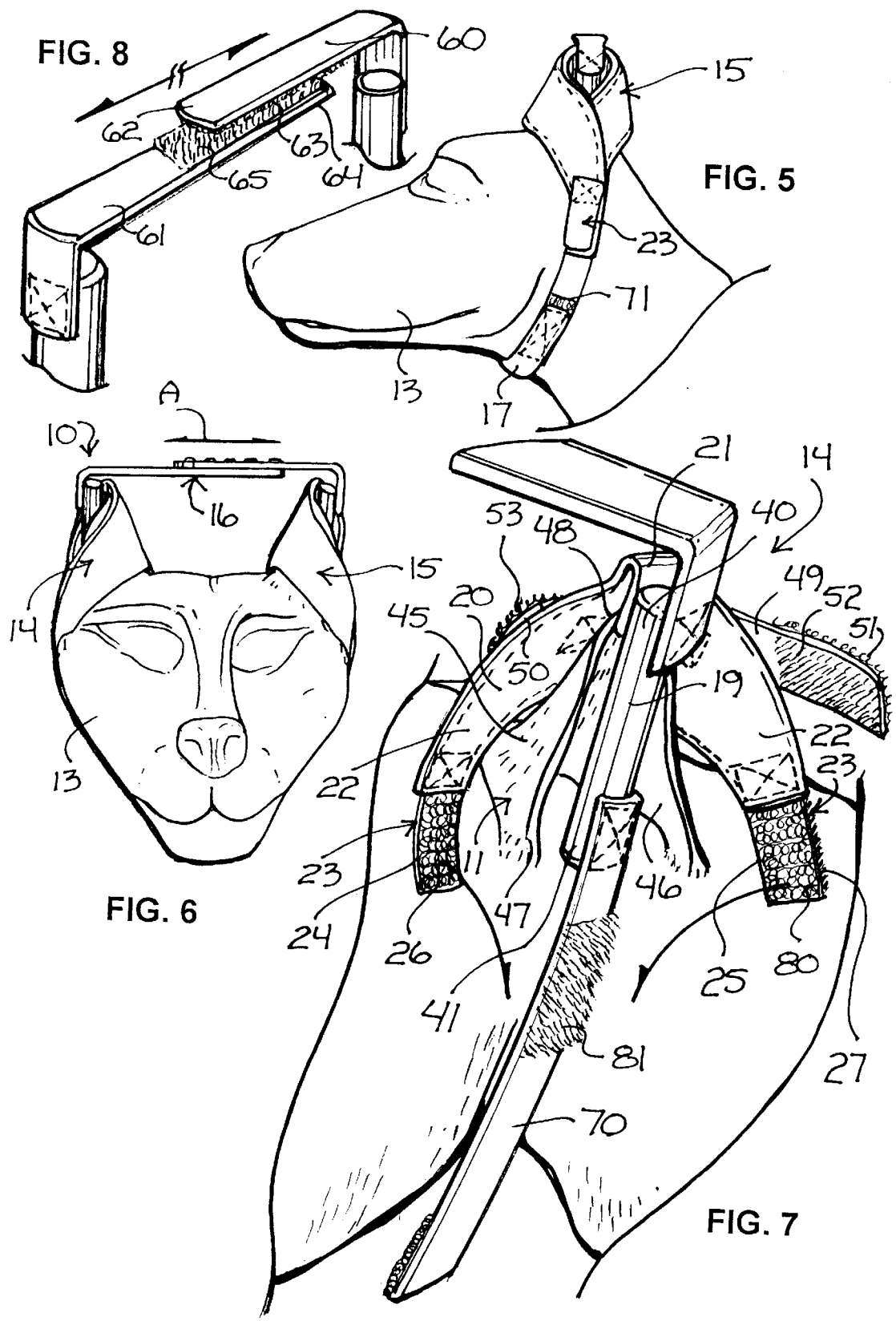

US 6,314,961 B1

ADJUSTABLE EAR SUPPORT APPARATUS

FIELD OF THE INVENTION

This invention relates to post operative care devices and, more particularly, to apparatus for supporting and protecting newly cropped ears of an animal.

BACKGROUND OF THE INVENTION

Some species of dogs normally have their ears cropped shortly after birth. The purpose of ear cropping is primarily aesthetic. After cropping, veterinarians fasten supporting structure to the newly cropped ears for protection and to force them to stand up during the healing process. The veterinarian normally contains this supporting structure in bandages that require periodic replacing at significant cost to the pet owner. To eliminate the necessity of repeated visits to the veterinarian to replace the bandages and support structure, skilled artisans have contrived a variety of devices specifically designed to support and protect newly cropped ears. Although exemplary, these devices are expensive and difficult use, install and construct. Because of these and other deficiencies, the continued need for improvement in the art is evident.

Accordingly, it would be highly desirable to provide improved apparatus for supporting and protecting newly cropped ears of an animal.

It is a purpose of the present invention to provide new and improved apparatus that is easy to construct.

It is another purpose of the present invention to provide new and improved apparatus that is easy to use.

It is still another purpose of the present invention to provide new and improved apparatus that is easy to install.

It is a further purpose of the present invention to provide new and improved apparatus that is inexpensive.

It is still a further purpose of the present invention to provide new and improved apparatus that is adjustable for accommodating the different sizes of the ears and heads of animals.

It is yet still a further purpose of the present invention to provide new and improved apparatus that is safe and efficient for intended use.

SUMMARY OF THE INVENTION

The above problems and others are at least partially solved and the above purposes and others realized in new and improved apparatus for supporting and protecting newly cropped ears of an animal. In a specific embodiment, apparatus of the invention comprises first and second ear support apparatus each engagable with one of the newly cropped ears and a bridge interconnecting the first ear support apparatus with the second ear support apparatus. The bridge is adjustable for adjusting the distance between the first and second ear support apparatus. The bridge comprises first and second bridge elements each extending from one of the first and second ear support apparatus, engagement apparatus carried by one of the first and second bridges and detachably engagable complemental engagement apparatus carried by the other one of the first and second bridges for adjustment of the first and second ear support apparatus in a reciprocal direction.

Each ear support apparatus includes a backing sized to substantially cover the outer surface of a newly cropped ear, a substantially rigid spine supported by the backing to extend from the base to the free end of the newly cropped ear adjacent the inner surface and an engagement assembly carried by the backing for securing the backing around the newly cropped ear and the spine in a wrapped condition. The backing preferably includes adjustable structure for adjusting the backing to conform substantially to the outer surface of a newly cropped ear. The adjustable structure comprises one or more removable segments positioned to face the base of the newly cropped ear. The invention may further include a strap supported by the first and second ear support apparatus for engagement about the head of the animal.

BRIEF DESCRIPTION OF THE DRAWINGS

The foregoing and further and more specific objects and advantages of the invention will become readily apparent to those skilled in the art from the following detailed description taken in conjunction with the drawings in which:

FIG. 5 is a side view of the apparatus of FIG. 1 shown as it would appear worn;

FIG. 6 is a front view of the apparatus of FIG. 1 shown as it would appear worn;

FIG. 7 is a perspective view of one of the ear support apparatus of FIG. 1 shown as it would appear being installed with an ear of the animal;

FIG. 8 is a perspective view of an embodiment of a bridge of the invention; and

DETAILED DESCRIPTION OF A PREFERRED EMBODIMENT

The present invention provides, among other things, new and improved apparatus for supporting and protecting newly cropped ears of an animal. Ensuing embodiments are easy to construct, easy to use and install, and incorporate structure for adjusting the apparatus to fit dogs having heads and ears of varying size.

Figure 1:
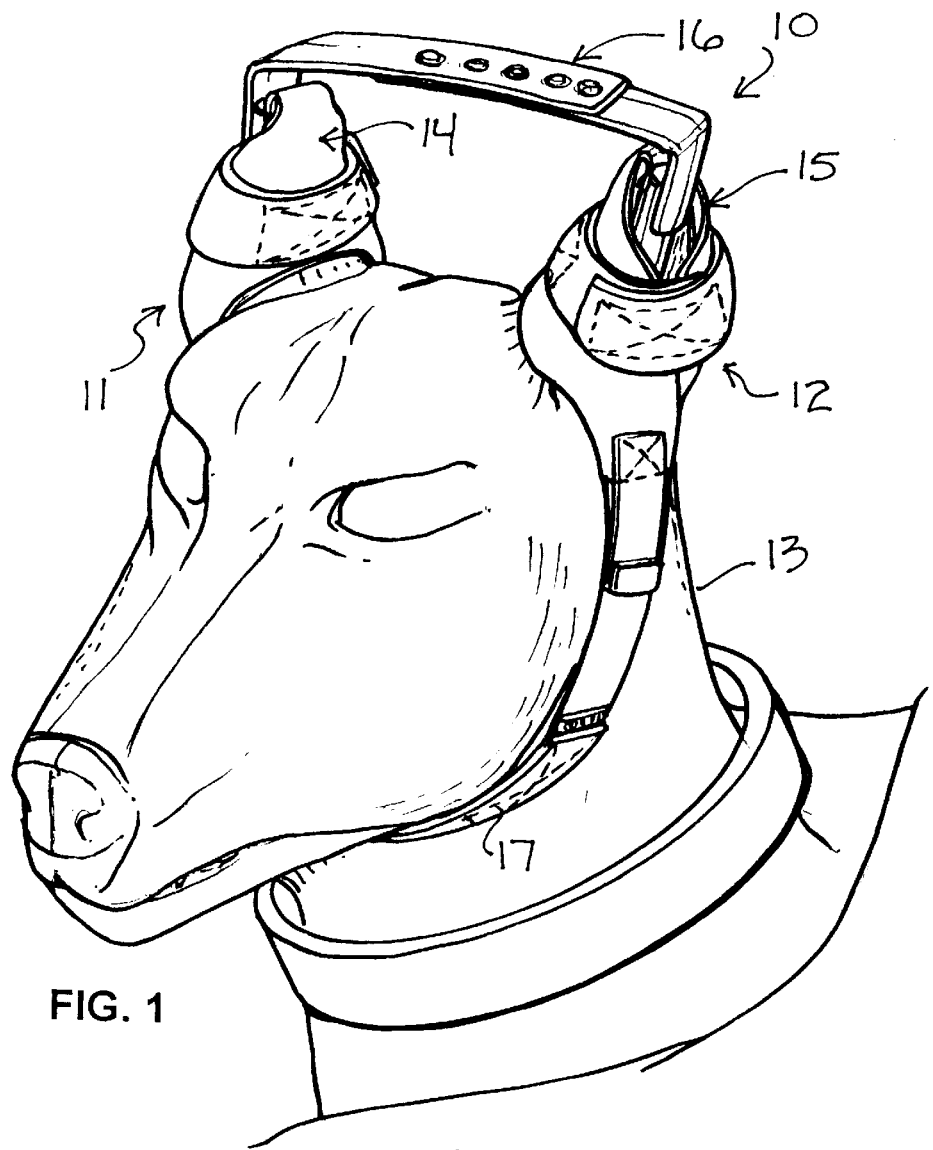
FIG. 1 is a perspective view of apparatus shown as it would appear worn to support and protect newly cropped ears of an animal, the apparatus including a bridge adjustably interconnecting a pair of ear support apparatus each mounted to one of the newly cropped ears, each ear support apparatus comprising a spine and a backing engagable with an ear and the spine in a wrapped condition.
Figure 2:
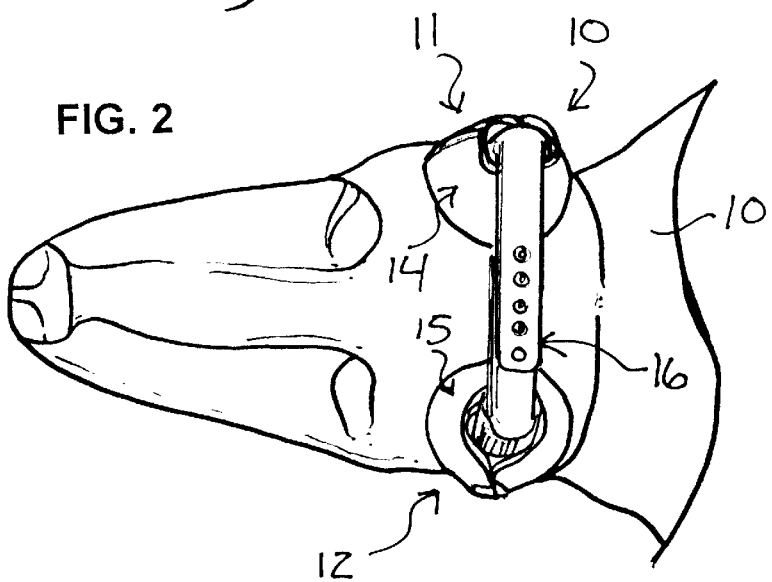
FIG. 2 is a top view of the apparatus of FIG. 1 shown as it would appear worn.

Turning now to the drawings, in which like reference characters indicate corresponding elements throughout the several views, FIGS. 1 and 2 are perspective views of apparatus 10 shown as it would appear worn to support and protect newly cropped ears 11 and 12 of an animal 13. Apparatus 10 is comprised of three main parts including a pair of ear support apparatus 14 and 15 adjustably interconnected with a bridge 16. To secure apparatus 10 in place to an animal's head, the invention may further include a strap 17 (not shown in FIG. 2) supported by the pair of ear support apparatus 14 and 15 and engagable about the animal's head extending from its ears to beneath the animal's lower jaw. Other strap arrangements may be used as desired for securing apparatus 10 to an animal's head.

Figure 3:
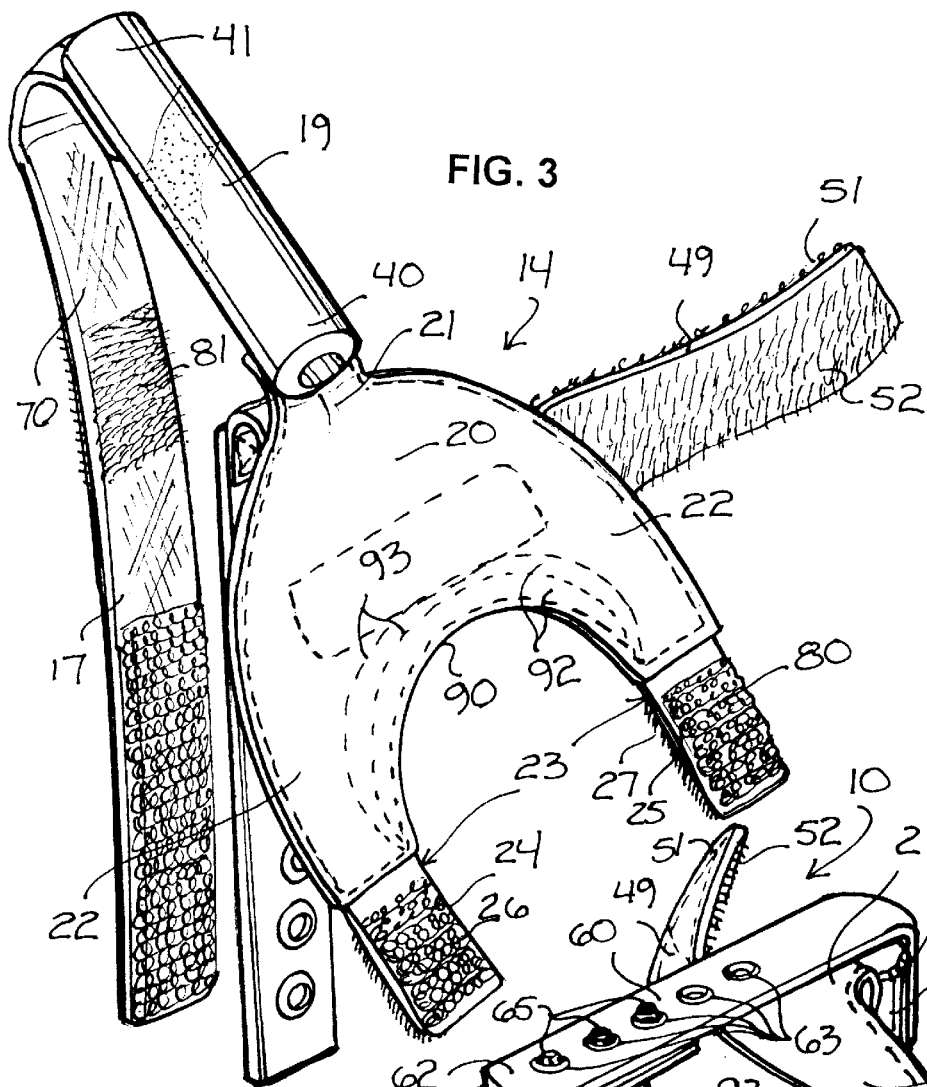
FIG. 3 is a perspective view of one of the ear support apparatus of FIG. 1.

Turning to FIG. 3, shown is a perspective view of ear support apparatus 14. Ear support apparatus 14 is comprised of a substantially rigid spine 19 and a backing 20 having a proximal extremity 21 and a distal extremity 21. Backing 20 is preferably constructed of a substantially pliant material such as nylon, cotton, canvass, polypropylene, etc., for allowing it to be moved into a wrapped condition about an ear. Distal extremity 22 supports an engagement assembly 23 comprising a pair of straps 24 and 25 that extend outwardly from distal extremity 22 in spaced and substantially parallel relation. Strap 24 supports an engagement element 26 that faces in a direction and strap 25 supports a detachably engagable complemental engagement element 27 that faces in an opposing direction. In this embodiment, engagement element 26 includes one of a hook medium and a loop medium and complemental engagement element includes the other one of the hook medium and the loop medium, an engagement pair commonly found under the exemplary trademark VELCRO ™. Although this hook and loop engagement pair is preferred, snap, button or other varieties of engagement pairs may be used. Preferably constructed of plastic or other similar substantially rigid material, spine 19 is elongate and includes an end 40 fixed to proximal extremity 21. Spine 19 extends away from proximal extremity 21 and terminates with a free end 41. Proximal extremity 21 may be sewn or glued to end 40.

Reference is now drawn to FIG. 7, which illustrates the installation of ear support apparatus 14 with newly cropped ear 11. Ear 11 includes an outer surface 45, an inner surface 46, projects outwardly from a base 47 and terminates with a free end 48. To install ear support apparatus 14, spine 19 is placed in an upright condition adjacent inner surface 46 with its free end 41 directed against base 41 and end 40 positioned adjacent free end 48 of ear 11. Spine 19 is preferably constructed of a length at least substantially equal to or somewhat greater than the length of a cropped ear. Backing 20 is folded down along the outer surface 45 of ear 11 with proximal extremity 21 located adjacent free end 48 of ear 11 and distal extremity 22 located adjacent base 47. From outer surface 45, backing 20 is then folded around the ear 11 and spine 19 in a wrapped condition and straps 24 and 25 joined in an overlapping state to engage engagement element 26 with complemental engagement element 27. To provide a more aggressive engagement, apparatus 10 may include a belt 49. Belt includes an end 50 fastened to backing 20, either sown or glued, between proximal extremity 21 and distal extremity 22. Belt 49 extends horizontally and terminates with a free or distal end 51. Belt 49 carries an engagement element 52 at end 51 and a detachably engagable complemental engagement element 53 at end 50. From the outer surface 45 of ear, end 51 may be wrapped around spine 19 and mated with end 50 in an overlapping state to engage engagement element 52 with complemental engagement element 53. Consistent with a preferred embodiment, engagement element 52 comprises one of a hook medium and a loop medium and complemental engagement element 53 comprises the other one of the hook medium and the loop medium, an engagement pair commonly found under the exemplary trademark VELCRO ™. However, snap, button or other conventional engagement pairs may be employed.

Figure 4:
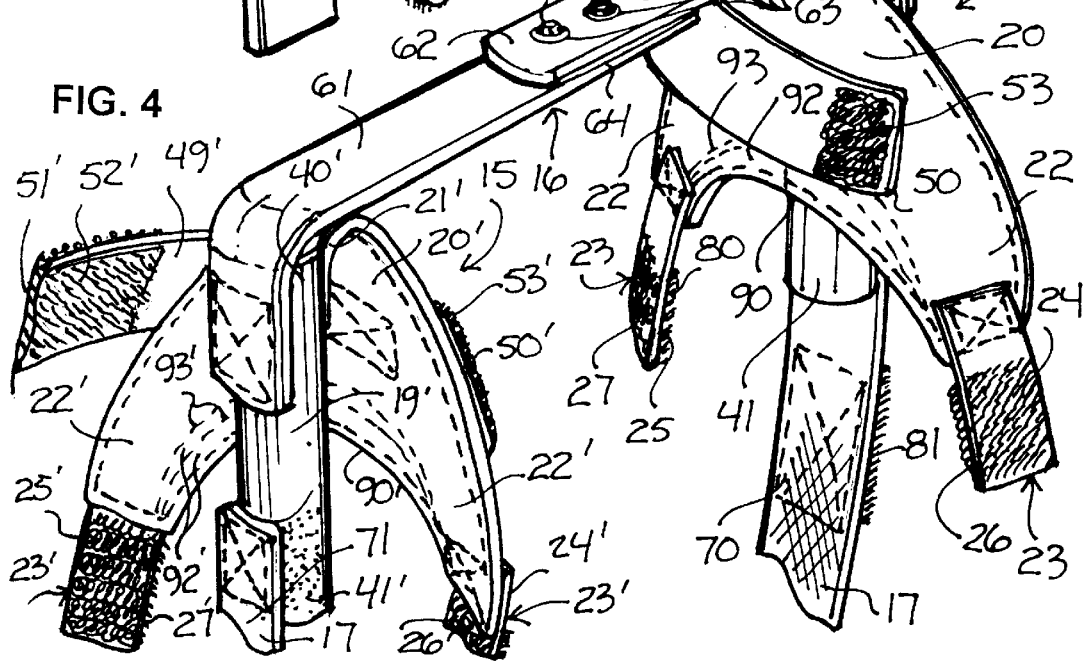
FIG. 4 is a fragmented perspective view of the apparatus of FIG. 1.

Turning to FIG. 4, the structure of ear support apparatus 15 is the mirror image of ear support apparatus 14. Having the same structural and functional attributes as ear support apparatus 14, ear support apparatus 15 will not be discussed in the interests of brevity and economy. For the purposes of orientation, however, the structural elements of ear support apparatus 15 will be briefly noted with the same reference characters used to describe ear support apparatus 14. In the interests of clarity, identical reference characters used to describe ear support apparatus 15 will include a prime ("'") symbol. In this regard, and like ear support apparatus 14, ear support apparatus 15 includes spine 19' having ends 40' and 41', backing 20', proximal extremity 21', distal extremity 22' engagement assembly 23', straps 24' and 25', engagement element 26', complemental engagement element 27', belt 49' including ends 50' and 51', engagement element 52' and complemental engagement element 53'.

With ear support apparatus 14 and 15 each mounted with one of newly cropped ears 11 and 12, respectively, as shown in FIGS. 1, 2 and 6, bridge 16 interconnects ear support apparatus 14 with ear support apparatus 15. Bridge 16 is adjustable for varying the distance between ear support apparatus 14 and 15. This is important because the distance or spacing between dogs' ears differs among the various dog breeds. Small dogs have a small spacing between their ears and large dogs have a larger spacing between their ears. The adjustable bridge 16 therefore allows a user to orient ear support apparatus 14 and 15 in a desired spacing in accordance with the space between the ears of a given animal, and to orient the ears in a desired upright orientation whether inwardly, outwardly or straight up.

In the embodiment shown in FIG. 4, bridge 16 is comprised of bridge elements 60 and 61 that, with ear support apparatus 14 and 15 each engaged with one of the ears of an animal, confront or otherwise face one another. Preferably constructed of flexible or substantially rigid plastic or the like, bridge element 60 is fixed to, and extends outwardly from, spine 19 proximate end 40 and terminates with a free end 61. Bridge element 60 can be sewn or glued to spine 19, and supports engagement apparatus 63 that, in this embodiment, comprises one of a plurality of snap elements/apertures and a plurality of complemental snap elements/protuberances positioned at spaced intervals along a length of bridge element 60 leading to free end 62. Preferably constructed of flexible or substantially rigid plastic or the like, bridge element 61 is fixed to, and extends outwardly from, spine 19' proximate end 40' and terminates with a free end 64. Bridge element 61 can be sewn or glued to spine 19', and supports complemental engagement apparatus 65 that, in this embodiment, comprises the other one of a plurality of snap elements/apertures and a plurality of complemental snap elements/protuberances positioned at spaced intervals along a length of bridge element 61 leading to free end 64. By selective engagement of engagement apparatus 63 with complemental engagement apparatus 65, the distance between ear support apparatus 14 and 15 may be adjusted and controlled along a reciprocal path or direction as generally indicated by the double arrowed line A in FIG. 6.

The snap element/aperture and complemental snap element/protuberance structure disclosed in combination with bridge 16 comprise a common engagement set or pair readily found among baseball caps. Snap, button or other suitable engagement pairs or sets may be used if so desired. As an example, FIG. 8 illustrates engagement apparatus 63 provided as one of a hook medium and a loop medium and complemental engagement apparatus 65 as the other one of the hook medium and the loop medium, an engagement pair commonly found under the exemplary trademark VELCRO ™.

As previously discussed, apparatus 10 may be secured in place to an animal's head with strap 17. In the embodiment shown in FIG. 4, strap 17 includes a pair of strap segments 70 and 71 each constructed of nylon, cotton, canvas or other substantially flexible material. Strap segment 70 is fixed to, and extends outwardly from, spine 19 proximate end 41 and terminates with a free end. Strap segment 70 can be sewn or glued to spine 19, and supports engagement apparatus of an engagement pair. Strap segment 71 is fixed to, and extends outwardly from, spine 19' proximate end 41' and terminates with a free end. Strap segment 71 can be sewn or glued to spine 19', and supports complemental engagement apparatus of the engagement pair of the strap 17. This engagement pair supported by strap segments 70 and 71 provides the desired engagement and may, of course, comprise a hook and loop engagement pair or perhaps a snap, button or buckle engagement pair or set.

Each backing 20 and 20' may, if desired, be provided with engagement apparatus for engaging complemental engagement apparatus supported by strap 17. When engaged with newly cropped ears 11 and 12, the ability to secure each backing 20 and 20' with strap 17 inhibits the ability of the animal to claw or tear away apparatus 10, and allows a user to provide each backing 20 and 20' with tension for added ear support and ear orientation. Regarding ear support apparatus 14 in FIG. 4, strap 25 carries engagement apparatus 80 that opposes its complemental engagement element 27, and strap segment 70 carries complemental engagement apparatus 81 located, in this specific example, at a position spaced a short distance from end 41 of spine 19. With ear support apparatus 14 properly engaged with a newly cropped ear and straps 24 and 25 engaged in the overlapping state, engagement apparatus 80 will substantially confront complemental engagement apparatus 81 which, of course, allows them to be engaged. Engagement and complemental engagement apparatus 80 and 81 may be provided as a hook and loop engagement pair as shown, or perhaps a snap, button or other suitable engagement set or pair. Engagement apparatus 80 and complemental engagement apparatus 81 may also be provided with ear support apparatus 15 in the same manner as ear support apparatus 14, further details of which will not be discussed in the interests of brevity.

In summary, the present invention provides exemplary apparatus for providing support and protection to newly cropped ears. The structure allowing the distance between ear support apparatus 14 and ear support apparatus 15 allows apparatus 10 to be fitted with all types of dogs, regardless of the distance between the ears. Furthermore, each backing 20 and 20' is constructed of a size that will substantially cover the outer surface of a newly cropped ear and conform substantially to the height of a newly cropped ear. For comfort as shown in FIGS. 3 and 4, distal extremity 22 defines a curved or arcuate central portion 90 that extends substantially from strap 24 to strap 25, and distal extremity 22' defines a similarly curved or arcuate central portion 90' that extends substantially from strap 24' to strap 25'. Each central portion 90 and 90' is shaped to conform substantially to the base of a newly cropped ear at the point where the base meets the animal's head. Because the distance between the free end and the base of a cropped ear can vary between dogs, each backing 20 and 20' desirably supports one or more segments 92 and 92' that comprise and form each central portion 90 and 90'. Each backing 20 and 20' is shown having two segments arranged in series leading toward proximal extremity 21 and 21', respectively. However, less or more may be provided. Segments 92 and 92' are each divided by arcuate perforate lines 93 and 93' formed into or with each backing 20 and 20'. From this construction and arrangement, one or more of segments 92 and 92' may be grasped and torn away at perforate lines 93 and 93' for adjusting the surface area of each backing 20 and 20' as needed so that each may be made to conform substantially with the outer surface of a newly cropped ear and the height of a newly cropped ear.

Figure 9:
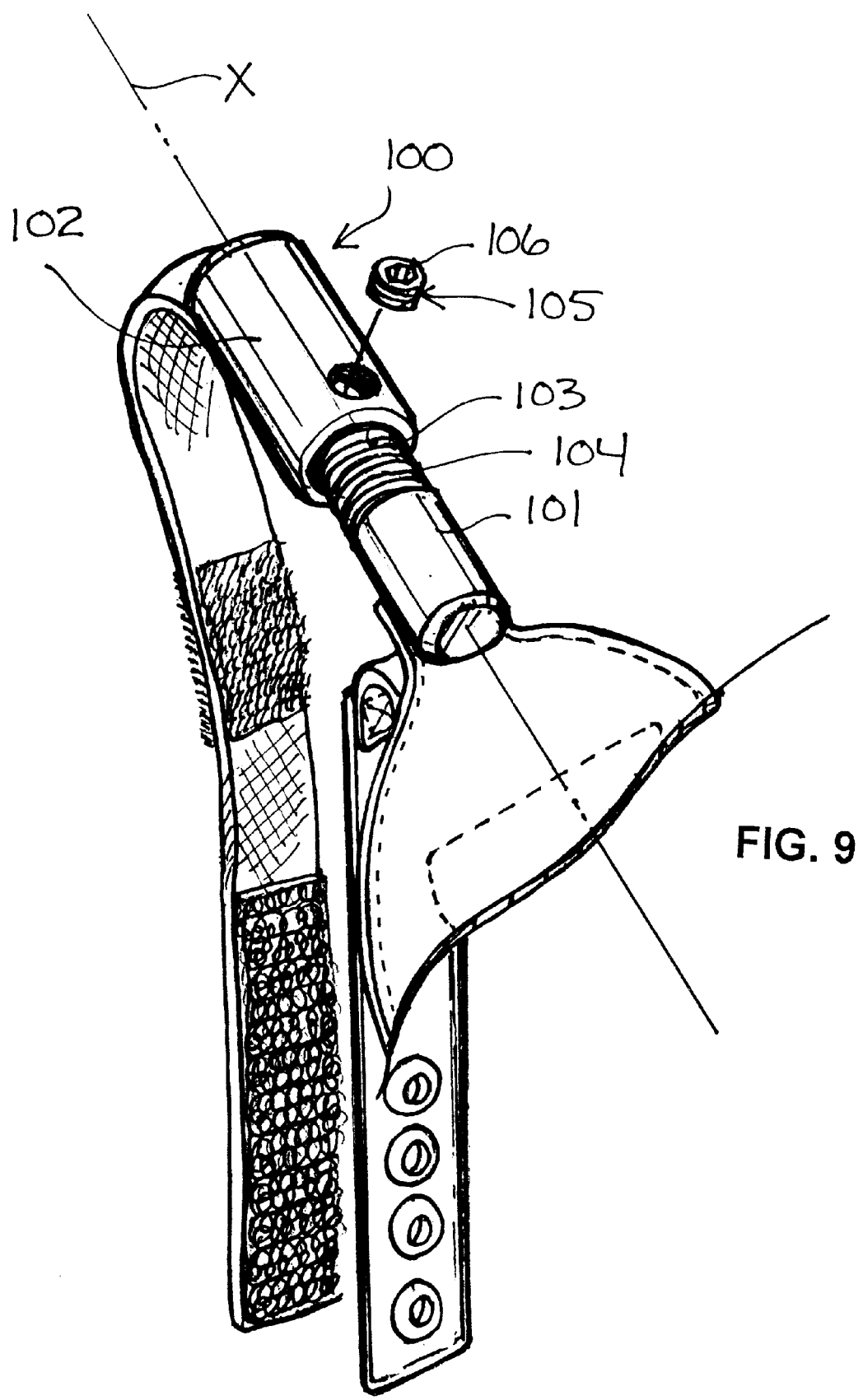
FIG. 9 is a perspective view of an embodiment of a spine of the invention.

To further provide each ear support apparatus 14 and 15 with height adjustment ability, FIG. 9 illustrates an embodiment of a spine 100 of the invention that may be used in lieu of spine 19 and/or spine 19'. Spine 100 defines a longitudinal axis X and is comprised of an assembly including a substantially rigid dowel 101 mounted partially in a substantially rigid sleeve 102 for adjustment in a reciprocally linear direction for allowing adjustment of the length of spine along its axis X. In this embodiment, sleeve 102 supports internal threads 103 threadably engaged with external threads 104 carried by dowel 101. Upon exertion of a rotational force to one or both of dowel 101 and sleeve 102, the length of spine 100 may be controlled and adjusted to conform substantially with the height of a newly cropped ear. Sleeve 102 carries a locking element 105 movable substantially in a reciprocally linear direction in opposition to dowel 101 for locking dowel 101 against sleeve 102 in a locked condition for securing spine 100 into a desired length. In this embodiment, locking element 105 comprises a threaded bolt 106 movable in reciprocal directions upon application of a rotational force. Of course other suitable structure may be employed with guide sleeve 102 for locking dowel 101 with sleeve 102 and for permitting the adjustment of the length of spine 100. In FIG. 9, dowel 101 is shown directed toward, and coupled to, a backing of the invention, and sleeve 102 is shown directed toward, and coupled to, one of the strap segments of the invention. Those of ordinary skill will appreciate that the positioning of dowel 101 and sleeve 102 may be reversed.

The present invention has been described above with reference to one or more preferred embodiments. However, those skilled in the art will recognize that changes and modifications may be made in the described embodiments without departing from the nature and scope of the present invention. Various changes and modifications to the embodiment herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. Apparatus for supporting and protecting newly cropped ears of an animal comprising:
   first and second ear support apparatus each engagable with one of the newly cropped ears;
   first and second bridge elements each extending from one of the first and second ear support apparatus;
   engagement apparatus carried by one of the first and second bridge elements; and
   detachably engagable complemental engagement apparatus carried by the other one of the first and second bridge elements.

2. Apparatus of claim 1, wherein the engagement apparatus comprises a hook medium.

3. Apparatus of claim 2, wherein the complemental engagement apparatus comprises a loop medium.

4. Apparatus of claim 1, wherein the engagement apparatus comprises a plurality of snap elements.

5. Apparatus of claim 4, wherein the complemental engagement apparatus comprises a plurality of complemental snap elements.

6. Apparatus of claim 1, further including a strap supported by the first and second ear support apparatus for engagement about the head of the animal.

7. Apparatus for supporting and protecting a newly cropped ear of an animal that projects outwardly from a base and terminates with a free end, the newly cropped ear including outer and inner surfaces, the apparatus comprising:
- a backing sized to substantially cover the outer surface of the newly cropped ear;
- a substantially rigid spine supported by the backing to extend from the base to the free end of the newly cropped ear adjacent the inner surface; and
- an engagement assembly carried by the backing for securing the backing around the newly cropped ear and the spine in a wrapped condition, the engagement assembly comprising:
  - first and second straps extending from the backing,
  - an engagement element carried by one of the first and second straps, and
  - a detachably engagable complemental engagement element carried by the other one of the first and second straps.

8. Apparatus of claim 7, wherein the engagement element includes a hook medium.

9. Apparatus of claim 8, wherein the detachably engagable complemental engagement element includes a loop medium.

10. Apparatus of claim 7, wherein the backing includes adjustable structure for adjusting the backing to conform substantially to the outer surface of the newly cropped ear extending from its base to its free end.

11. Apparatus of claim 10, wherein the adjustable structure includes a removable segment positioned to face the base of the newly cropped ear.

12. Apparatus of claim 11, wherein the segment is removable along a perforate line formed into the backing.

13. Apparatus of claim 10, wherein the adjustable structure includes a plurality of removable segments positioned to face the base of the newly cropped ear.

14. Apparatus of claim 13, wherein each segment is removable along one of a plurality of perforate lines formed into the backing.

15. Apparatus for supporting and protecting a newly cropped ear of an animal that projects outwardly from a base and terminates with a free end, the newly cropped ear including outer and inner surfaces, the apparatus comprising:
- a support structure engagable to support and protect the newly cropped ear, the support structure including a backing an adjustable structure for adjusting the backing to conform substantially to the outer surface of the newly cropped ear; and
- a segment of the backing positioned to face the base of the newly cropped ear, wherein the segment is removable from the backing along a perforate line formed into the backing.

16. Apparatus for supporting and protecting newly cropped ears of an animal, each newly cropped ear having an outer surface, an inner surface and a base leading to a free end, the apparatus comprising:
- first and second backings each sized to substantially cover the outer surface of one of the newly cropped ears;
- first and second substantially rigid spines each supported by one of the first and second backings to extend from the base to the free end adjacent the inner surface of one of the newly cropped ears;
- first and second engagement assemblies each carried by one of the first and second backings for securing the first and second backings around one of the newly cropped ear and one of the first and second spines a wrapped condition;
- a strap supported by the first and second ear support apparatus for engagement about the head of the animal;
- engagement apparatus supported by each engagement assembly; and
- detachably engagable complemental engagement apparatus supported by the strap.

17. Apparatus of claim 16, wherein each of the first and second engagement assemblies comprises:
- first and second straps positioned for engagement in an overlapping state;
- an engagement element carried by one of the first and second straps; and
- a detachably engagable complemental engagement element carried by the other one of the first and second straps.

18. Apparatus of claim 17, wherein the engagement element includes a hook medium.

19. Apparatus of claim 18, wherein the detachably engagable complemental engagement element includes a loop medium.

20. Apparatus of claim 16, wherein the engagement apparatus comprises one of a hook medium and a loop medium.

21. Apparatus of claim 20, wherein the complemental engagement apparatus comprises the other one of the hook medium and the loop medium.

22. Apparatus of claim 16, wherein each one of the first and second substantially rigid spines comprises a dowel mounted partially in a sleeve for adjustment in a reciprocally linear direction.

23. Apparatus for supporting and protecting a newly cropped ear of an animal that projects outwardly from a base and terminates with a free end, the newly cropped ear including outer and inner surfaces, the apparatus comprising:
- a support structure engagable to support and protect the newly cropped ear, the support structure including a backing; and
- a plurality of segments of the backing positioned to face the base of the newly cropped ear, wherein each segment is removable along one of a plurality of perforate lines formed into the backing.

* * * * *